(12) United States Patent
Daraio et al.

(10) Patent No.: US 8,327,709 B2
(45) Date of Patent: Dec. 11, 2012

(54) METHOD AND APPARATUS FOR NONDESTRUCTIVE EVALUATION AND MONITORING OF MATERIALS AND STRUCTURES

(75) Inventors: Chiara Daraio, Pasadena, CA (US); Piervincenzo Rizzo, Pittsburgh, PA (US)

(73) Assignees: University of Pittsburgh, Pittsburgh, PA (US); California Institute of Technology, Pasadena, CA (US)

( * ) Notice: Subject to any disclaimer, the term of this patent is extended or adjusted under 35 U.S.C. 154(b) by 937 days.

(21) Appl. No.: 12/251,164

(22) Filed: Oct. 14, 2008

(65) Prior Publication Data

US 2009/0204344 A1  Aug. 13, 2009

Related U.S. Application Data

(60) Provisional application No. 61/063,903, filed on Feb. 7, 2008, provisional application No. 61/124,920, filed on Apr. 21, 2008.

(51) Int. Cl.
*G01N 29/06* (2006.01)
*G01N 29/24* (2006.01)

(52) U.S. Cl. ............................................ 73/632; 73/642

(58) Field of Classification Search .................. 73/11.01, 73/11.02, 12.01, 12.04, 12.05, 12.06, 12.11, 73/12.13, 12.14, 627, 629, 632, 642
See application file for complete search history.

(56) References Cited

U.S. PATENT DOCUMENTS

| | | | |
|---|---|---|---|
| 2,729,094 A | 1/1956 | Piety | 73/1.85 |
| 3,724,260 A | 4/1973 | Bole | 73/12.13 |
| 4,116,041 A | 9/1978 | Tholen et al. | 73/12.13 |
| 4,711,754 A | 12/1987 | Bednar | |
| 5,085,081 A * | 2/1992 | Ohno | 73/620 |
| 5,165,270 A | 11/1992 | Sansalone | |
| 5,497,649 A | 3/1996 | Ambur et al. | 73/12.06 |
| 5,736,642 A | 4/1998 | Yost | |
| 5,787,049 A * | 7/1998 | Bates | 367/7 |
| 5,841,019 A | 11/1998 | Drabrin | |
| 5,974,881 A * | 11/1999 | Donskoy et al. | 73/579 |
| 6,186,004 B1 * | 2/2001 | Kaduchak et al. | 73/596 |

(Continued)

FOREIGN PATENT DOCUMENTS

WO  2007/084318  7/2007

OTHER PUBLICATIONS

McCracken, Jennifer et al. "S.R.-22 Smart Pavement: Response Characteristics of a Jointed Plain Concrete Pavement to Applied and Environmental Loads," University of Pittsburgh, (Feb. 2008).

(Continued)

*Primary Examiner* — Daniel Larkin
*Assistant Examiner* — Rose M Miller
(74) *Attorney, Agent, or Firm* — Steinfl & Bruno LLP

(57) ABSTRACT

A method and apparatus for nondestructive evaluation (NDE) of structures and materials using a highly nonlinear medium for the generation and detection of one or multiple highly nonlinear pulses (or highly nonlinear waves) impinging on a material or structure. The apparatus includes pulse exciters that induce the propagation of highly nonlinear, weakly nonlinear or linear stress waves in the material, system, or structure to be inspected and/or detectors for the observation and the detection of the output waves from the material/structure being tested. The NDE method includes the use of the tunable highly nonlinear apparatus as impulse exciter alone, or in combination with an accelerometer or a nonlinear sensor to detect the outgoing pulse.

8 Claims, 10 Drawing Sheets

U.S. PATENT DOCUMENTS

| | | | |
|---|---|---|---|
| 6,418,081 | B1 | 7/2002 | Sen |
| 6,799,126 | B1 | 9/2004 | Ratcliffe |
| 6,843,957 | B2 | 1/2005 | Statnikov |
| 7,191,656 | B2 | 3/2007 | Yagi et al. ................. 73/579 |
| 2004/0064047 | A1* | 4/2004 | Marmarelis et al. .......... 600/437 |
| 2005/0072236 | A1 | 4/2005 | Heyman |
| 2006/0144146 | A1 | 7/2006 | Hedberg |
| 2006/0207913 | A1 | 9/2006 | Hong |
| 2006/0225509 | A1 | 10/2006 | Haupt |
| 2009/0229910 | A1 | 9/2009 | Daraio |
| 2010/0024519 | A1 | 2/2010 | Zhang ........................ 73/12.01 |

OTHER PUBLICATIONS

Daraio, C.; Nesterenko, V.F.; Herbold, E., and Jin, S. "Pulse mitigation by a composite discrete medium". *Journal De Physique IV Proceedings DYMAT 2006. 8th International Conference on Mechanical and Physical Behavior of Materials under Dynamic Loading*, J. Phys. IV France 134,473-479, Dijon, France (2006).

Grote, K., Hubbard, S., Harvey, J., and Rubina, Y., "Evaluation of infiltration in layered pavements using surface GPR reflection techniques," *Journal of Applied Geophysics* 57 (2005) 129-153 (2005).

Lanza di Scalea, F., Rizzo, P., and Seible F., "Stress Measurement and Defect Detection in Steel Strands by Guided Stress Waves," *ASCE Journal of Materials in Civil Engineering*, vol. IS (3), pp. 211-304 (2003).

Nesterenko, V.F.; Lazaridi, A.N. and Sibiryakov, E.8. The decay of soliton at the contact of two "acoustic vacuums". *Prikl. Mekh. Tekh. Fiz.* 2, 19-22 (1995) [*J. Appl. Mech. Tech. Phys.* 36, 166-168 (1995)].

Tinkey, Y., and Olson, L.D. "Non-Destructive Evaluation Method for Determination of Internal Grout Conditions Inside Bridge Post-Tensioning Ducts Using Rolling Stress Waves for Continuous Scanning," *NCHRPIDEA Program Project Final Report, Publisher: Transportation Research Board*, http://pubsindex.trb.org/documentlview/default.asp?Ihid=80 1832). (2007).

M Sansalone, N. J Carino, *Impact-Echo: A Method for Flaw Detection in Concrete Using Transient Stress Waves*, NBSIR 86/3452, National Bureau of Standards, (NTIS PB 87-1044441 AS). (1986).

Del Duce, A. and Killey, R.I. Comparison of Nonlinear Pulse Interactions in 160-Gb/s Quasi-Linear and Dispersion Managed Soliton Systems. Journal of Lightwave Technology, vol. 22, No. 5, pp. 1263-1271 (2004).

Daraio, C., Nesterenko, V.F., "Highly nonlinear contact interaction and dynamic energy dissipation by forest of carbon nanotubes," *Applied Physics Letters*, vol. 85, No. 23, pp. 5724-5726 (Dec. 7, 2004).

PCT International Search Report for PCT/US2009/032954 filed on Feb. 3, 2009 in the name of California Institute of Technology et al.

PCT Written Opinion for PCT/US2009/032954 filed on Feb. 3, 2009 in the name of California Institute of Technology et al.

PCT International Search Report for PCT/US2008/079860 filed on Oct. 14, 2008 in the name of California Institute of Technology et al.

PCT Written Opinion for PCT/US2008/079860 filed on Oct. 14, 2008 in the name of California Institute of Technology et al.

Arancibia-Bulnes, C.A. and Ruiz-Suarez, J.C. Broad solitons in homogeneous Hertzian granular chains, Physica D, 168, pp. 159-160, (2002).

Benson, D.J., Nesterenko, V.F. Anomalous decay of shock impulses in laminated composites, Journal of Applied Physics, 89, pp. 3622-3626, (2001).

Coste, C. and Gilles, B. On the validity of Hertz contact law for granular material Acoustics, European Physical Journal B, 7, 155 (1999).

Coste, C., Falcon, E., & Fauve, S. Solitary waves in a Chain of Beads under Hertz contact, Phys. Rev. E, 56, 6104-6117 (1997).

Daraio, C.; Nesterenko, V.F.; Jin, S. Strongly nonlinear waves in 3D phononic crystals, APS—Shock Compression of Condensed Matter, AIP Conference Proceedings, Portland (OR), pp. 197-200 (2003).

Daraio, C.; Nesterenko, V.F.; Herbold, E.; Jin, S. Energy Trapping and Shock Disintegration in a Composite Granular Medium, Phys. Rev. Lett.; 96, 058002, (2006).

Daraio, C. and Nesterenko, V.F. Propogation of highly nonlinear signals in a two dimensional network of granular chains, 1419-1422, Amer. Institute of Physics, (2007).

Daraio, C.; Nesterenko, V.F.; Herbold, E.; Jin, S.Strongly nonlinear waves in a chain of Teflon beads. Physical Review E 72, 016603 (2005).

Daraio, C.; Nesterenko, V.F. Strongly nonlinear waves in a chain of polymer coated steel beads. Physical Review E; 73, 026612, (2006).

Daraio, C.; Nesterenko, V.F.; Herbold, E.; Jin, S. "Strongly nonlinear waves in polymer based phononic crystals". APS—Shock Compression of Condensed Matter, 1507-1510, AIP Conference Proceedings, Baltimore (MD), (2006).

Daraio, C.; Nesterenko, V.F.; Herbold, E.; Jin, S. Tunability of solitary wave properties in one dimensional strongly nonlinear phononic crystals, Phys. Rev. E; 73, 026610. (2006).

Dash, P.C., and Patnaik, K. Solitons in nonlinear diatomic lattices. Progress in Theoretical Physics, 65, pp. 526-541, (1981).

Doney, R. and Sen, S. Decorated, Tapered, and Highly Nonlinear Granular Chain, Phys. Rev. Lett. 97, 155502, (2006).

Doney, R. and S. Sen, Impulse absorption by tapered horizontal alignments of elastic spheres, 041304, Phys. Rev. E 72, (2005).

Goddard, J.D. Nonlinear Elasticity and Pressure-Dependent Wave Speeds in Granular Media, Proc. R. Soc. Lond. A 430, 105, (1990).

Goldenberg, C. and Goldhirsch, I. Friction enhances elasticity in granular solids, Nature, 435, 188-191, (2005).

Hascoët, E. and Herrmann, H.J. Shocks in Non-loaded bead chains with impurities. Eur. Phys. J. B 14, 183-190, (2000).

Herbold, E.B.; Nesterenko, V.F.; Daraio, C. Influence of Controlled Viscous Dissipation on the Propagation of Strongly Nonlinear Waves in Stainless Steel Based Phononic Crystals. APS—SCCM, 1523-1526, AIP Conference Proceedings, Baltimore (MD), (2006).

Herbold, E.B. Shock wave structure in a strongly nonlinear lattice with viscous dissipation, Phys. Rev. D 75, 021304 (2007).

Herbold E.B., Nesterenko V.F., Solitary and shock waves in discrete strongly nonlinear double power-law materials, Applied Physics Letters, 90, 261902, (2007).

Hinch E. J. and Saint-Jean, S. The fragmentation of a line of balls by an impact, Proc. R. Soc. A 455, 3201, (1999).

Hong, J. & Xu, A. Nondestructive identification of impurities in granular medium. Appl. Phys. Lett., 81, 4868-4870, (2002).

Hong, J. Universal power-law decay of the impulse energy in granular protectors. Phys. Rev. Lett. 94, 108001, (2005).

Hostler, S.R., Brennen, C.E. Pressure wave propagation in a granular bed, Physical Review E, 72, 3, 031303, (2005).

Korteweg, D.J., and de Vries, G. On the change of form of long waves advancing in a rectangular canal, and on a New type of long stationary Waves. London, Edinburgh and Dublin Philosophical Magazine and Journal of Science, ser. 5, 39, pp. 422-443, (1895).

Lambert, R. F. and Tesar, J.S. Acoustic structure and propagation in highly porous, layered, fibrous materials. Journal of the Acoustical Society of America, 76, 1231-1237, (1984).

Lazaridi, A.N. and V.F. Nesterenko, Observation of new type of solitary waves in a one-dimensional granular medium, J. Appl. Mech. Tech. Phys. 26, pp. 405-408, (1985).

Manciu, F.S., Sen, S. Secondary solitary wave formation in systems with generalized Hertz interactions. Physical Review E 66, 016616. (2002).

Melo F, Job S, Santibanez F, et al. Experimental evidence of shock mitigation in a Hertzian tapered chain, Physical Review E 73, 4, 041305. (2006).

Nakagawa, M. et al. Impulse dispersion in a tapered granular chain Gran. Matt. 4, pp. 167-174, (2003).

Nesterenko, V. F., Daraio, C., Herbold, E. B. and Jin, S. Anomalous wave reflection at the interface of two strongly nonlinear granular media. Physical Review Letters 95, 158702, (2005).

Nesterenko, V.F., Propagation of nonlinear compression pulses in granular media, J. Appl. Mech. Tech. Phys. 5, pp. 733-743, (1984).

Rosas, A., Romero, A.H., Nesterenko, V.F., Lindenberg, K. Observation of Two-Wave Structure in Strongly Nonlinear Dissipative Granular Chains. Physical Review Letters, 98, 164301, (2007).

Rosas, A. and Lindenberg, K. Pulse velocity in a granular chain. Phys. Rev. E 69, 037601, (2004).

Rosenau P. and Hyman J.M. Compactions: Solitons with Finite Wavelength, Phys. Rev. vol. 70, No. 5, 564-567, (1993).

Sansalone, M. and Streett W. B. Impact-Echo Nondestructive Evaluation Concrete and Masonry, Bullbrier Press, ISBN: 0-96-12610-6-4, (1997).

Sen, S., Manciu, M., & Manciu, F.S. Ejection of ferrofluid grains using nonlinear acoustic impulses. Appl. Phys. Lett., 75, 10, 1479-1481, (1999).

Sen et al. Impulse Backscattering Based Detection and Imaging of Buried Objects in Granular Beds, SPIE 4394, 607, (2001).

Sen, S. and Manciu, M. Solitary wave dynamics in generalized Hertz chains: An improved solution of the equation of motion, Physical Review E, 64, pp. 056605, (2001).

Sen, S., Manciu, M., Wright J.D. Solitonlike pulses in perturbed and driven Hertzian chains and their possible applications in detecting buried impurities. Phys. Rev. E, 57, 2, 2386-2397, (1998).

Sen et al. Using mechanical energy as a probe for the detection and imaging of shallow buried inclusions in dry granular beds, Intl Journal of Modern Physics B, vol. 19, 2951-2973, (2005).

Sinkovits, R.S. and S. Sen, Nonlinear dynamics in granular columns, Phys. Rev. Lett. 74, pp. 2686-2689, (1995).

Sokolow A, Bittle EG, Sen, S. Solitary wave train formation in Hertzian chains, European Physics Letters, 77, 2, 24002, (2007).

Somfai E, Roux JN, Snoeijer JH, et al. Elastic wave propagation in confined granular systems Physical Review E 72, 2, 021301, (2005).

Vergara, L. Scattering of Solitary Waves from Interfaces in Granular Media. Phys. Rev. Lett. 95, 108002, (2005).

Jinying Zhu et al Imaging concrete structure using air-coupled impact-echo, J. Engineering Mechanics, 628-640, (Jun. 2007).

Carino, N.J. "Stress Wave Propagation methods," Chapter 14 of Malhotra, V.M. and Carino N.J. "Handbook on nondestructive testing of concrete CRC Press" (1991).

Job, S., Melo, F. Sen, S. & Sokolow, A. "How Hertzian solitary waves interact with boundaries in a 1D granular medium," Phys. Rev. Lett., 94, 178002, (2005).

Hertz, H. Journal fur Die Reine and Angewandie Mathematic, 92, pp. 156-171 (1881).

Gilles, B. and Coste, C. "Nonlinear elasticity of a 2D regular array of beads," Powders and Grains, Proceedings of the Fourth International Conference on Micromechanics of Granular Media, Sendai, May 21-25, (2001).

Nesterenko, V.F., Daraio, C., Herbold, E.B., Jin, S., Anomalous wave reflection at the interface of two strongly nonlinear granular media, The American Physical Society, Physical Review Letters PRL 95, 158702 (Published electronically Oct. 6, 2005).

Porter, M.A., Daraio, C., Herbold, E.B., Szelengowicz, I., Kevrekidis, P.G., Highly nonlinear solitary waves in periodic dimer granular chains, The American Physical Society, Physical Review E 77, 015601 (Published electronically Jan. 28, 2008).

PCT International Search Report for PCT/US2009/032958 filed on Feb. 3, 2009 in the name of California Institute of Technology and Chiara Daraio, et al.

PCT Written Opinion for PCT/US2009/032958 filed on Feb. 3, 2009 in the name of California Institute of Technology and Chiara Daraio, et al.

Nesterenko, V.F. *Dynamics of Heterogeneous Materials*, Chap. I, Springer-Verlag, NY (2001).

Office Action issued by USPTO for U.S. Appl. No. 12/364,947 dated Aug. 31, 2011.

Notice of Allowance issued by USPTO for U.S. Appl. No. 12/364,974 dated Jun. 23, 2011.

Rizzo, P. and Lanza di Scalea, F. *"Load Measurement and Health Monitoring in Cable Stays via Guided Wave Mangetostrictive Ultrasonics"*, Materials Evaluations, vol. 62, No. 10, pp. 1057-1064 (2004).

Goldsmith, W., *Impact. The Theory and Physical Behavior of . . .* , Edward Arnold Press, London, pp. 24-50 (1965).

Ambati, M., Fang, N., Sun, C., and Zhang, X. *"Surface resonant states and superlensing in acoustic metamaterials"*, Physical Review B, vol. 75, pp. 195447-1-195447-5 (2007).

Cain, C.A., and Umemura, S., *"Concentric-Ring and Sector-Vortex Phased-Array Applicators for Ultrasound Hyperthermia"*, IEEE Transactions on Microwave Theory and Techniques, vol. MIT-34., No. 5, pp. 542-551, (May 1986).

Carretero-Gonzalez, R., Kharti, D., Porter, M.A., Kevrekidis, P.G. and Daraio, C., *"Dissipative Solitary Waves in Periodic Granular Media"*, Physical Review Letters, pp. 1-5, (2008).

Chatterjee, A., *"Asymptotic solution for solitary waves in a chain of elastic spheres"*, Physical Review E, vol. 59, No. 5, pp. 5912-5919, (May 1999).

Clement, G.T., *"Perspectives in clinical uses of high-intensity focused ultrasound"*, Ultrasonics, vol. 42, pp. 1087-1093, (2004).

Daraio, C., Nesterenko, V.F., Aubuchon, J.F. and Sungho, J., *"Dynamic Nanofragmentation of Carbon Nanotubes"*, Nano Letters, vol. 4, No. 10, pp. 1915-1918, (2004).

Daraio, C., Nesterenko, V.F., Jin, S. Wang, W. and Rao, A.M., *"Impact response by a foamlike forest of coiled carbon nanotubes"*, Journal of Applied Physics, vol. 100, pp. 064309-1-064309-4, (2006).

Daraio, C. and Nesterenko, V.F., *"Strongly nonlinear wave dynamic in a chain of polymer coated beads"*, Physical Review E, vol. 73, pp. 026612-1-026612-7, (2006).

Doney, R.L. and Sen, S., *"Impulse absorption by tapered horizontal alignments of elastic spheres"*, Physical Review E, vol. 72, pp. 041304-1-041304-11, (2005).

Ebbini, E.S. and Cain, C.A., *"Multiple-Focus Ultrasound Phased-Array Pattern Synthesis: Optimal Driving-Signal Distributions for Hyperthermia"*, IEEE Transactions on Ultrasonics, Ferroelectronics and Frequency Control, vol. 36, No. 5, pp. 540-548, (Sep. 1989).

Fink, M., *"Time Reversal of Ultrasonic Fields—Part I Basic Prinicples"*, IEEE Transactions on Ultrasonics, Ferroelectronics and Frequency Control, vol. 39, No. 5, pp. 540-548, (Sep. 1992).

Fok, L., Ambati, M. and Zhang, X., *"Acoustic Metamaterials"*, MRS Bulletin, vol. 33, pp. 931-935, (Oct. 2008).

Fraternali, F., Porter, M.A. and Daraio, C., *"Optimal Design of Composite Granular Protectors"*, Mechanics of Advanced Materials and Structures, vol. 17, pp. 1-17, (2010).

Ter Haar, G., *"Ultrasound Focal Beam Surgery"*, Ultrasound in Med. & Biol., vol. 21, No. 9, pp. 1089-1100, (1995).

Hakansson, A., Cervera, F., and Sanchez-Dehesa, *"Sound focusing by flat acoustic lenses without negative refraction"*, Applied Physics Letters, vol. 86, pp. 054102-1-054102-3, (2005).

Herbold, E.B. Kim, J., Nesterenko, V.F., Wang, S. and Daraio, C., *"Tunable frequency band-gap and pulse propagation in a strongly nonlinear diatomic chain"* Acta Mechnica, pp. 1-38, (2009).

Holt, R.G., Roy, R.A., Edson, P.A. and Yang, X., *"Bubbles And HIFU: The Good, The Bad, And The Ugly"* pp. 120-131, (2002).

Hong, J., Kim, H. and Hwang, J-P, *"Characterization of soliton damping in the granular chain under gravity"*, Physical Review E, vol. 61, No. 1, pp. 964-967, (2000).

PCT International Search Report mailed on Sep. 29, 2011 for PCT Application PCT/US2011/026371 filed on Feb. 25, 2011 in the name of California Institute of Technology et al.

Job, S., Melo, F., Sokolow, A. and Sen, S., *"Solitary wave trains in granular chains: experiments, theory and simulations"*, Granular Matter, vol. 10, pp. 13-20, (2007).

Johnson, K.L., *"Contact Mechanics"*, Contact Mechanics, Cambridge University Press, Cambridge, MA, pp. 1-17, (2005).

Khatri, D., Daraio, C. and Rizzo, P., *"Highly Nonlinear Waves' Sensor Technology for Highway Infrastructures"*, SPIE Smart Structures/NDE, 15th Annual International Symposium, San Diego, CA (2008).

Krim, H. and Viberg, M., *"Two Decades of Array Signal Processing Research"*, IEEE Signal Processing Magazine, pp. 67-94, (1996).

Kushibiki, J. and Chubachi, N., *"Material Characterization by Line-Focus-Beam Acoustic Microscope"*, IEEE Transaction on Sonics and Ultrasonics, vol. SU-32, No. 2, pp. 189-212, (1985).

Lalonde, R. and Hunt, J.W., *"Variable Frequency Field Conjugate Lenses for Ultrasound Hyperthermia"*, IEEE Transactions on Ultrasonics, Ferroelectronics and Frequency Control, vol. 42, No. 5, pp. 825-831, (Sep. 1995).

Lalonde, R., Worthington, A., and Hunt, J.W., "*Field Conjugate Acoustic Lenses for Ultrasound Hyperthermia*", 1991 Ultrasonics Symposium, pp. 1339-1342, (1991).

Li, J., Fok, L., Yin, X., Bartal, G. and Zhang, X., "*Experimental demonstration of an acoustic magnifying hyperlens*", Nature Materials, vol. 8, pp. 931-934, (2009).

Manciu, M., Tehan, V.N. and Sen, S., "*Dynamics of a gravitationally loaded chain of elastic beads*", Chaos, vol. 10, No. 3, pp. 658-669, (2000).

Porter, M.A., Daraio, C., Szelengowicz, I., Herbold, E.B. and Kevrekidis, P.G., "*Highly nonlinear solitary waves in heterogeneous periodic granular media*", Physica D, vol. 238, pp. 666-676, (2009).

Nesterenko, V.F., "*Nonlinear Impulses in Particulate Materials*", in Dynamics of heterogeneous materials, Spring-Verlag, New York, NY, pp. 1-135, (2001).

Ocheltree, K.B., Benkeser, P.J., Frizzelli, L.A. and Cain, C.A., "*An Ultrasonic Phased Array Applicator for Hyperthermia*", IEEE Transactions on Sonics and Ultrasonics, vol. SU-31, No. 5, pp. 526-531, (1984).

Ponomarenko, S.A., and Agrawal, G.P., "Linear optical bullets", Optics Communications, vol. 261, pp. 1-4, (2006).

Porter, M.A., Daraio, C., Szelengowicz, I., Herbold, E.B. and Kevrekidis, P.G., "*Highly Nonlinear Solitary Waves in Periodic Dimer Granular Chains*", Physical Review E, vol. 77, pp. 1-5, (2008).

Rosas, A. and Lindenberg, K., "*Pulse propagation in chains with nonlinear interactions*", Physical Review E, vol. 69, pp. 016615-1-016615-4, (2004).

Sadd, M.H., Tai, A. and Shukla, A., "*Contact Law Effects on Wave Propagation in Particulate Materials using Distinct Element Modeling*", Int. J. Non-linear Mechanics, vol. 28, No. 2, pp. 251-265, (1993).

Sen, S., Visco, D.P. and Mohan, T.R., "*Impulse Backscattering based Detection and Imaging of Shallow Buried Objects*", Mat. Res. Soc. Symp. Proc., vol. 759, pp. MM2.9.1-MM2.9.8, (2003).

Sen, S., Hong, J., Bang, J., Avalos, E. and Doney, R., "*Solitary waves in the granular chain*", Physics Reports, vol. 462, pp. 21-66, (2008).

Shukla, A., Sadd, M.H., Xu, Y. and Tai, Q.M., "*Influence of Loading Pulse Duration on Dynamic Load Transfer in a Simulated Granular Medium*", J. Mech. Phys. Solids, vol. 41, No. 11, pp. 1795-1808, (1993).

Silberberg, Y., "*Collapse of optical pulses*", Optics Letters, vol. 15, No. 22, (1990).

Sukhovich, A., Jing, L. and Page, J.H., "*Negative refraction and focusing of ultrasound in two-dimensional phononic crystals*", Physical Review B, vol. 77, pp. 014301-1-014301-9, (2008).

Turnbull, D.H., and Foster, F.S., "*Beam Steering with Pulsed Two-Dimensional Transducer Arrays*", IEEE Transactions on Ultrasonics, Ferroelectrics, and Frequency Control, vol. 38, No. 4, pp. 320-333, (1991).

Van Trees, H.L., "*Optimum Array Processing—Part IV of Detection, Estimation, and Modulation Theory*", John Wiley & Sons, pp. 1-32, (2008).

Van Veen, B.D. and Buckley, K.M., "*Beamforming: A Versatile Approach to Spatial Filtering*", IEEE ASSP Magazine, pp. 4-24, (1988).

PCT Written Opinion mailed on Sep. 29, 2011 for PCT Application PCT/US2011/026371 filed on Feb. 25, 2011 in the name of California Institute of Technology et al.

Yang, S., Page, J.H., Liu, Z., Cowan, M.L., Chan, C.T. and Sheng, P., "*Focusing of Sound in a 3D Phononic Crystal*", Physical Review Letters, vol. 93, No. 2, pp. 024301-1-024301-4, (2004).

Zhang, X. and Liu, Z., "*Superlenses to overcome the diffraction limit*", Nature Materials, vol. 7, pp. 436-441, (2008).

Zhu, Y., Sienkiewicz, F., Shukla, A. and Sadd, M., "*Propagation of Explosive Pulses in Assemblies of Disks and Spheres*", J. of Engineering Mechanics, pp. 1050-1059, (1997).

First Office Action issued on Nov. 24, 2011 for Chinese Application No. 200880126412.2 filed on in the name of California Institute of Technology et al.

Restriction Requirement mailed on Jul. 1, 2011 for U.S. Appl. No. 12/364,947, filed Feb. 3, 2009 in the name of Chiara Daraio et al.

Hakansson, A., et al., Acoustic lens design by genetic algorithms, Physical Review B 2004, 70: 214302-1-214302-9.

\* cited by examiner

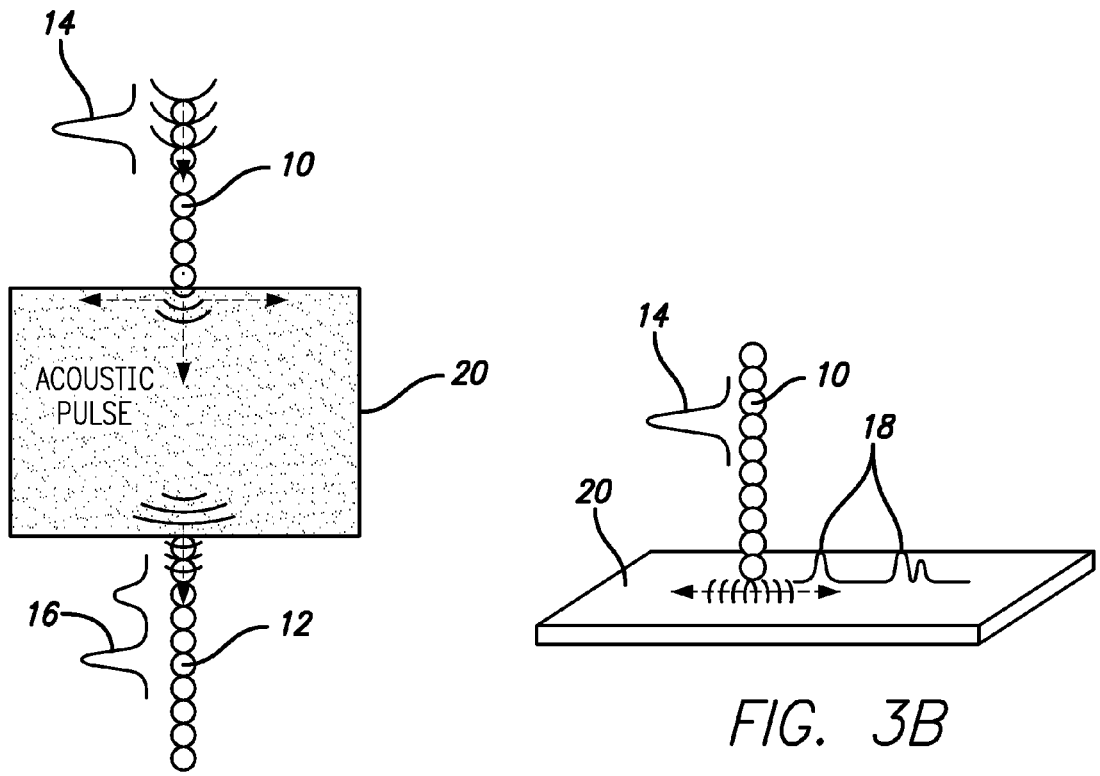
FIG. 3A
FIG. 3B
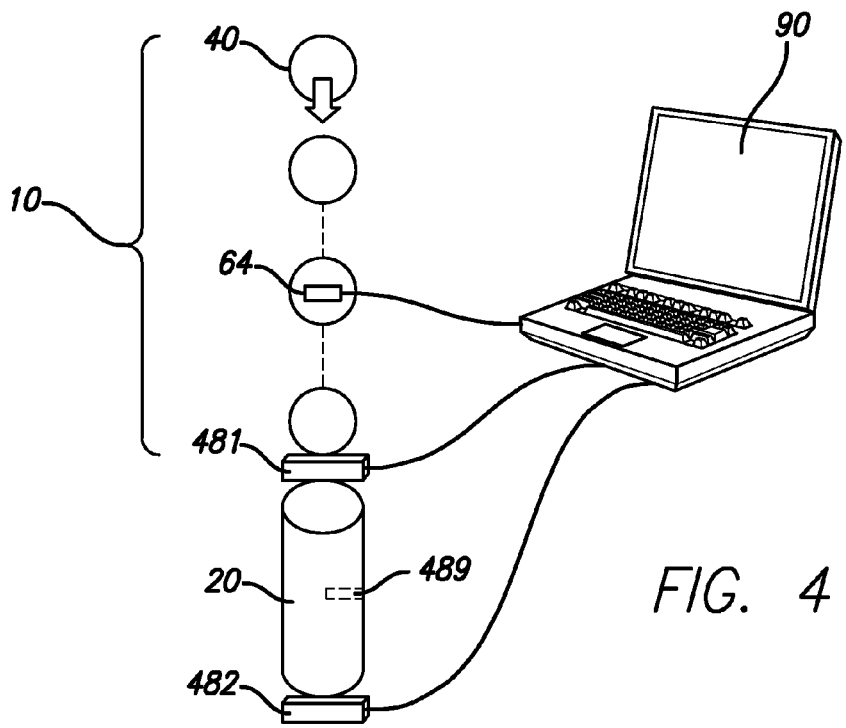
FIG. 4

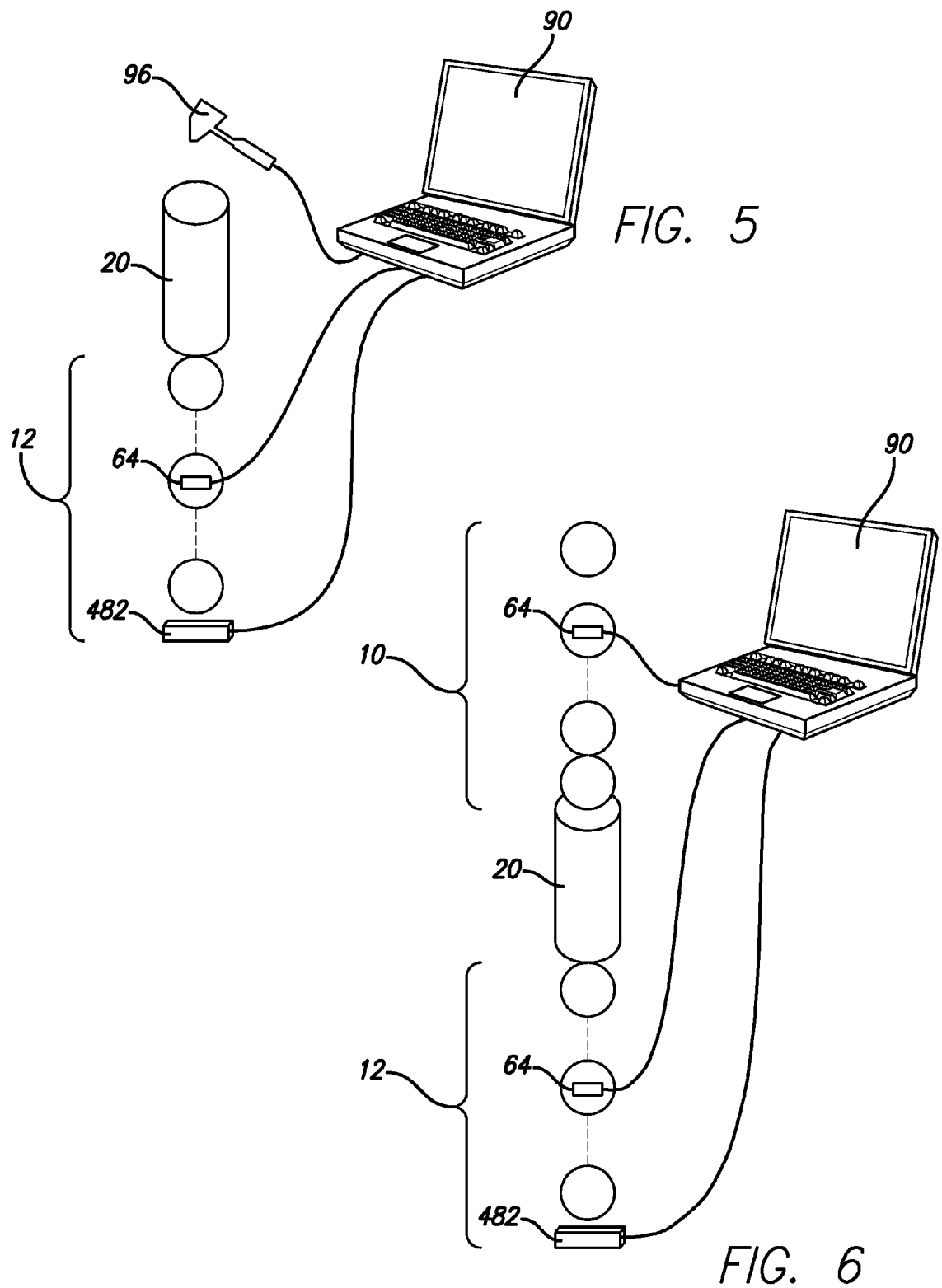

METHOD AND APPARATUS FOR NONDESTRUCTIVE EVALUATION AND MONITORING OF MATERIALS AND STRUCTURES

CROSS-REFERENCE TO RELATED APPLICATIONS

STATEMENT REGARDING FEDERALLY SPONSORED RESEARCH OR DEVELOPMENT

This invention was made with government support under Grant No. CMMI0825345 awarded by the National Science Foundation. The government has certain rights in the invention.

BACKGROUND

1. Field

This disclosure relates to a method and apparatus for the excitation and transmission of highly nonlinear pulses with selectable pulse properties into a structure or material and the detection of such pulses from the structure or material. More particularly, the present disclosure describes a method and apparatus for exciting a selectable number of controllable highly nonlinear pulses with desired shapes, amplitudes, frequencies and/or durations, which may then be used for non-destructive evaluations and/or structural health monitoring.

2. Description of Related Art

Non-destructive evaluation of a material or structure may be accomplished through the use of impact testing. In impact testing, the material or structure is typically struck with an impact device and sound waves propagating through the material or structure are then measured to provide some indication of defects within the material or structure. See, for example, U.S. Pat. No. 5,165,270 to Sansalone, et al., dated Nov. 24, 1992. In U.S. Pat. No. 5,165,270, the impact device is a number of differently weighted spheres that are each designed to produce a different duration of impact, thereby imparting different stress waves into the structure to be tested. The different stress waves have different frequency values depending on the impact duration. Each sphere is disposed on one end of a spring-steel rod. At the start of the test, a selected sphere is in a resting position. The sphere is withdrawn from the rest position by a pair of jaws to a given height above the structure. This action deflects the spring-steel rod, thus increasing the potential energy of the impact sphere. At a predetermined release point, the sphere is released causing it to impact the structure and impart a given energy to the structure. The impact produces stress (sound) waves that are reflected from the external surfaces and/or internal defects of the structure. The reflected waves are detected by a transducer that converts the normal surface displacements caused by the waves into an electrical signal. The electrical signal is then processed to provide an amplitude/frequency spectrum indicative of either the thickness of the structure or the defects disposed therein.

Other impact testing apparatus and techniques are known in the art, but generally use approaches similar to that described above, i.e., strike the material to be tested and measure the stress wave propagation. The impact devices (i.e., strikers) used in impact-testing technology typically cost several hundreds of dollars or more and need coupling to a signal conditioner. Line-powered signal conditioners are used to power sensors and condition their output signals for transmittal to readout and recording instruments. Impact hammers are used for delivering impulse forces into test specimens and the signal conditioner is used to provide electrical measurement signals of the amplitude and frequency content of the applied force. Hammers and conditioners used for non-destructive evaluation may be very expensive. Embodiments of the present invention as described below may provide for less costly apparatus for nondestructive evaluation of materials and structures.

SUMMARY

Embodiments of the present invention rely on the use of highly nonlinear waves (HNWs), including highly nonlinear solitary waves (HNSWs), which can form and travel in highly nonlinear systems (i.e., systems that may comprise granular, layered, fibrous or porous materials). Compared to conventional stress waves used in prior art systems using sonic-, ultrasonic-, or impact-based technology, HNWs offer significantly higher tunability in terms of wavelength, wave speed (proportional to the wave amplitude and to the material's properties), number of generated pulses, and amplitude control in a simple and reproducible setup that can be adjusted at will.

Embodiments of the present invention may provide for improvements over prior art systems that include: 1) larger tunability range of the frequency, amplitude and velocity of induced pulses resulting in a broader range of sizes of detectable cracks, defects, and inclusions in a material (i.e., multiscale defects sensitivity); 2) enhanced repeatability of measurements, improving a measurements system's reliability and avoiding the required high operator skills typically needed by prior art methods; 3) simpler and more scalable design of the instruments within the measurement system (such as wave actuators and sensors) to different dimensions (which may also provide more versatility of applications); 4) reduced power requirement characteristics of the instruments; and 5) reduced cost of assembling and manufacturing of the process components, sensors and actuators (up to 2 orders of magnitude lower than present commercially available impact hammers).

Some embodiments of the present invention comprise methods and apparatus for nondestructive evaluation and/or structural health monitoring (NDE/SHM) based on highly nonlinear sensors and/or actuators combined together (fully nonlinear system) or coupled with conventional sensing/actuating methods. For example, one embodiment comprises a NDE/SHM method in which a highly nonlinear actuator is used in combination with a classical receiver (such as an accelerometer, laser interferometer, piezogauge or other detectors known in the art), where the actuator provides an input to a material to be inspected and the classical receiver measures the output. Another embodiment comprises an NDE/SHM method in which classical impact echo/tap testing methods of actuation are used together with a highly nonlinear receiver, where the classical impact/tap test provide input and the highly nonlinear receiver measures the output. Still another embodiment comprises an NDE/SHM method in which a highly nonlinear actuator and a highly nonlinear receiver are used together, where the actuator provides the input and the receiver measures the output.

An embodiment of the present invention is a method for performing an inspection of an element or structure comprising: generating one or more highly nonlinear waves; directing the one or more highly nonlinear waves into the element or structure to be inspected; and, detecting pulses deriving from the waves directed into the element or structure after the waves have propagated through at least a portion of the element or structure to be inspected.

Another embodiment of the present invention is a system for inspecting an element or structure comprising: a highly nonlinear wave actuator, wherein the actuator is configurable to impinge highly nonlinear pulses to the element or structure to be inspected, and a pulse detector configurable to detect pulses from the actuator propagating through at least a portion of the element or structure to be inspected.

Still another embodiment of the present invention is A method for performing an inspection of an element or structure comprising: generating an inspection pulse; directing the inspection pulse into the element or structure to be inspected; directing the inspection pulse after it has propagated through at least a portion of the element or structure to be inspected into a nonlinear receiver; and detecting the inspection pulse after it has propagated through at least a portion of the nonlinear receiver.

Still another embodiment of the present invention is A system for inspecting an element or structure comprising: a pulse actuator, wherein the actuator is configurable to apply pulses to the element or structure to be inspected, and a nonlinear receiver configurable to detect pulses from the actuator propagating through at least a portion of the element or structure to be inspected.

BRIEF DESCRIPTION OF THE SEVERAL VIEWS OF THE DRAWINGS

FIG. 3A is a schematic diagram representing the creation, propagation and detection of highly nonlinear solitary waves in relation to a bulk highly nonlinear, weakly nonlinear, or linear medium.

FIG. 3B is a schematic diagram representing the transmission of highly nonlinear waves in waveguide structures made of highly nonlinear, weakly nonlinear, or linear medium.

FIG. 4 depicts a system where a highly nonlinear actuator is used in combination with a classical receiver.

FIG. 5 depicts a system where a classical impact echo/tap testing hammer is used in combination with a highly nonlinear receiver.

FIG. 6 depicts a system where a highly nonlinear actuator is used in combination with a highly nonlinear receiver.

DETAILED DESCRIPTION

Figure 1A:
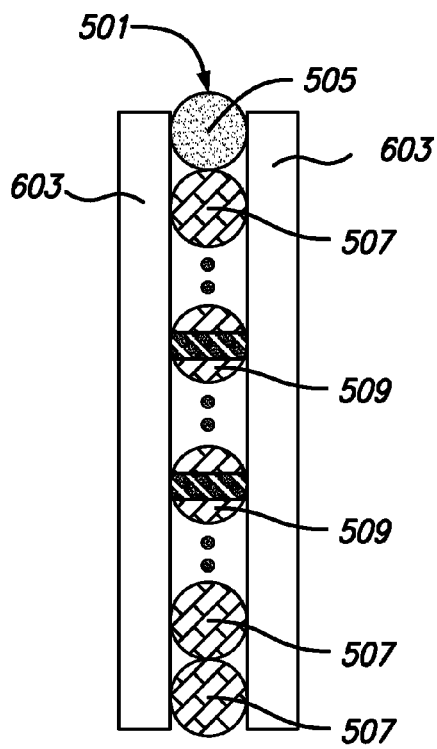
FIG. 1A shows a schematic representation of a system for production and/or detection of highly nonlinear waves.

Embodiments of the present invention provide for nondestructive evaluation and monitoring of materials and structures through the use of highly nonlinear pulses and waves generated in one dimensional chains of granular components. In this disclosure, the granular components or grains may comprise granular matter, which is defined as an aggregate of particles or layers in elastic contact with each other, preferably in linear or network shaped arrangements. While embodiments of the present invention use highly nonlinear pulses and waves, additional advantages may be provided when highly nonlinear solitary waves or pulses are used, generated, and/or detected. For purposes of this disclosure, highly nonlinear solitary waves are to be considered as a specific case of highly nonlinear waves. Additionally, highly nonlinear solitary pulses are to be considered as a specific case of highly nonlinear pulses. Hence, any references to highly nonlinear waves herein are to be considered as including highly nonlinear solitary waves and any references to highly nonlinear pulses herein are to be considered as including highly nonlinear solitary pulses unless otherwise denoted.

The contact interaction between the grains is regulated by the highly nonlinear force F—displacement δ relationship shown in Eq. 1:

$$F \approx A\delta^n \quad \text{(Eq. 1)}$$

where A is a material's parameter and n is the nonlinear exponent (with n>1). An unusual feature of the granular state is the negligible linear range of the interaction forces between neighboring particles resulting in zero sound speed in an uncompressed material. This makes the linear and weakly nonlinear continuum approaches based on Korteveg-de Vries (KdV) equation invalid and places granular materials in a special class according to their wave dynamics. The dynamic response of granular materials is controlled by the highly nonlinear wave theory that supports the formation and propagation of highly nonlinear compact solitary waves.

In granular materials composed by perfectly spherical beads, the highly nonlinear behavior stems from the dynamics of the contact interactions, regulated by Hertz law, for which the exponent n in Eq. 1 is equal to 1.5. This highly nonlinear response can also be found in many other nonlinear systems composed by grains with different geometries and the theoretical formulation has been extended and generalized to all nonlinear exponents n, with n≠1. For example, other geometries may include irregular grains with conical contacts where n=2; forests of vertically aligned carbon nanotubes where n=2.2; transverse vibration in a fiber with discrete particles where n=3 and plug chain gas-liquid systems where n=3. The continuum treatment of the highly nonlinear wave theory extends to periodic heterogeneous media, such as, granular systems where the particles composing the chain are not identical, and periodic defects alternate throughout its length.

Highly nonlinear solitary waves are stationary pulses forming in ordered granular media by the balancing effects of their geometric nonlinearity and the dispersion present in the medium. A unique feature of the highly nonlinear solitary waves (that makes them different from all other previous solitary waves or solitons described in various other physical systems, such as in fluids, atomistics and electromagnetic waves), is the independence of their wave width from their amplitude. For granular systems, in which Hertz law is valid and the exponent n=1.5, their spatial size is always 5 particles diameter, no matter what wave amplitude or wave speed is present in the system. Using the notation found in the most general treatment of the nonlinear wave theory, the wave equation for a uniform highly nonlinear system, derived from the Hertzian interaction law, is shown in Eq. 2 below:

$$u_{\tau\tau} = u_x^{n-1} u_{xx} + G u_x^{n-3} u_{xx}^3 + H u_x^{n-2} u_{xx} u_{xxx} + I u_x^{n-1} u_{xxxx} \quad (Eq. 7)$$

where u is the displacement, $\tau$ s a rescaled time, n is the nonlinear exponent found in Eq. 1 and the explicit expression of the parameters I, H, G can be found in Porter, M. A.; Daraio, C.; Herbold, E. B.; Szelengowicz, I.; Kevrekidis, P. G. "Highly nonlinear solitary waves in phononic crystal dimers" Physical Review E, 77, 015601(R), 2008. As shown in Porter et al, the expressions for G, H, and I are as follows:

$$G = D^2 \frac{(2 - 3k + k^2)m_1^2}{6(m_1 + m_2)^2},$$

$$H = D^2 \frac{2(k-1)(2m_1^2 + m_1 m_2 - m_2^2)}{6(m_1 + m_2)^2},$$

$$I = D^2 \frac{2(m_1^2 - m_1 m_2 + m_2^2)}{6(m_1 + m_2)^2}.$$

The solution for Eq. 2, describing the shape and properties of the highly nonlinear solitary waves, from direct integration is of the form shown in Eq. 3 below:

$$u_\xi = v = B \cos^{\frac{2}{n-1}}(\beta \xi), \quad (Eq. 3)$$

where $B = \left(\frac{\mu}{[\beta^2 s(s-1)]}\right)^{1/n-1}$, $\beta = \sqrt{\sigma} \frac{(1-\eta)}{2}$ and $s = pl$.

The generality of the highly nonlinear wave equation shown in Eq. 2 is given by the fact that it includes also the linear and weakly nonlinear regimes of wave propagation. These regimes can be extrapolated by adding an initial pre-strain (precompression) to the system. Its solution demonstrates that in a highly nonlinear medium only two harmonics contribute to a stationary mode of propagation of the periodic signal. The solitary shape, if the initial prestrain $\xi_0$ is approaching 0, can be taken as one hump of the periodic solution provided by Eq. 3 with finite wave length equal only to five particle diameters in the case of a Hertzian granular system. In analogy with the KdV solitons, the highly nonlinear solitary waves are supersonic, which means that their phase velocity is larger than the initial sound velocity ($c_0$) in the nonlinear medium (especially in the case of an uncompressed system, in which the $c_0$=0). For granular chains composed by spherical particles, the speed of the solitary wave $V_s$ as nonlinear function of the maximum particle dynamic strain can be expressed as shown in Eq. 4:

$$V_s = \frac{2}{\sqrt{5}} c \, \xi_m^{1/4} = 0.6802 \left(\frac{2E}{a \, \rho^{3/2}(1-\nu^2)}\right)^{1/3} F_m^{1/6}, \quad (Eq. 4)$$

where $F_m$ is the maximum dynamic contacts force between the particles in the discrete chain.

The relationship shown in Eq. 4 may provide for applications in the field of dynamics and acoustic properties of materials. Such waves, as predicted by the theory and validated numerically and experimentally, have tunability characteristics. By changing the mechanical and/or the geometrical properties of the high nonlinear medium supporting the formation of HNWs, the shape and the properties of the traveling pulse can be tuned. In other words, the properties of the nonlinear waves in the highly nonlinear media can be "engineered" for a specific application. These "controllable" waves may then be used as new boundary conditions in various structures for testing. It may also be desirable to generate a train of nonlinear waves rather than a single nonlinear pulse.

The analytical expression for the tunability of the solitary waves speed in a Hertzian system derived from the presence of added precompression and obtained from the discretization of the particles in the chain, is expressed as shown in Eq. 5 below:

$$V_s = \quad (Eq. 5)$$
$$0.9314 \left(\frac{4E^2 F_0}{a^2 \rho^3 (1-\nu^2)^2}\right)^{1/6} \frac{1}{(f_r^{2/3}-1)} \left\{\frac{4}{15}[3 + 2f_r^{5/3} - 5f_r^{2/3}]\right\}^{1/2}.$$

where $F_0$ represents the static prestress (precompression) added to the system, $f_r = F_m/F_0$ and $F_m$ is the maximum contacts force between the particles in the discrete chain.

The dependence of the solitary wave properties on the materials parameters is shown in Eq. 4 for a non-prestressed system and in Eq. 5 for a prestressed system. Also note that, with HNSWs, the system is size independent but sensitive to the presence of periodic heterogeneities in the chain. Therefore, the solitary waves may be scalable to various sizes, according to the needs of each specific application.

According to Eqs. 4 and 5, the tunability of the HNSWs can be achieved by varying one or more parameters of the nonlinear medium. For example, increasing the particle size of the highly nonlinear medium increases the wavelength and the wave speed and amplitude decrease. This tunability provides the possibility of reducing or eliminating the electronic equipment, such as function generators, necessary to excite stress waves of a given shape and wavelength. Therefore, embodiments of the present invention may reduce some of the power demands in ultrasonic actuation needed by prior art systems and may allow the use wireless technology instead of tethered technology known in the art. In addition, the high-sensitivity of wave amplitude and wave speed to the state of stress state in highly nonlinear material may also allow for improvements in the estimation of applied stress over that obtained by conventional acoustoelastic methods.

Embodiments of the present invention also allow for the use of particles having morphology different than the one described by the classical Hertzian shape (n=1.5), which can add another element to the tunability, that is by varying n in Eq. 1 the wavelength (and, therefore, the signal's frequency) will vary significantly. Further, a HNW or HNSW traveling in a system composed of alternating short chains of hard and soft beads (that can be interpreted as defects) or in any periodic heterogeneous system will induce significant changes in the properties of the traveling pulse. Systems composed of randomized assemblies of particles, such as chains including particles of different materials, masses and diameters in a disordered and quasi-disordered configuration, present thermalization phenomena that induce pulse decomposition and excitation of higher frequency modes.

The use of solitary waves for defect and impurity detection in granular media is discussed in Sen, S., Manciu, M., and Wright, J. D., "Solitonlike Pulses in Perturbed and Driven Hertzian Chains and Their Possible Applications in Detecting Buried Impurities," Phys. Rev. E, 57, no. 2, 2386-2397 (1998) and in Hong, J. & Xu, A., "Nondestructive identification of impurities in granular medium." Appl. Phys. Lett., 81, 4868-4870 (2002). Solitary waves have been demonstrated to be sensitive to the granular materials properties, such as elastic modules, and applied stress and the dependence of the velocity and shape of the backscattered signal on the presence of light and heavy impurities in a granular chain have also been noted. Highly nonlinear solitary pulses have been studied numerically and experimentally in various one-dimensional highly nonlinear systems assembled from chains of stainless-steel, glass, brass, nylon, polytetrafluoroethylene (PTFE) and Parylene coated steel beads. As predicted by the theoretical formulation, the numerical and experimental validation showed a significant difference in the speed and amplitude of the supported solitary waves as a function of the materials parameters.

The equations discussed above generally apply to HNSWs. However, embodiments of the present invention may rely upon the generation and/or detection of HNWs, treating the generation and/or detection of HNSWs as just a special case of HNWs. A schematic representation of a system for production and/or detection of HNWs is shown in FIG. 1A. In FIG. 1A, a chain 501 of particles or beads 505, 507, 509 is positioned between stays 603. By impinging the first particle 505 into the second particle 507, a HNW is generated (however, the generated HNW may stabilize into a HNSW). In this configuration, the first particle 505 may be considered as a striker particle. The wave propagates as long as the particles 505, 507, 509 stay in contact. Wavelength, speed, and amplitude of the wave can be tuned by selecting a desired combination of chain size (diameter and number of particles), particle material, and pre-compression on the particles. Some of the particles 509 may have embedded piezoelements or other detection apparatus that can be used to monitor the propagation of HNWs within the chain 501. The system shown in FIG. 1A can also be used for the detection of HNWs by coupling the system to a material or structure and using the detector particles 509 with the piezoelements to detect the waves.

Figure 1B:
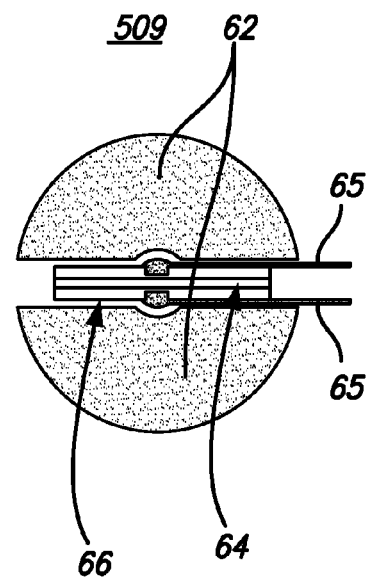
FIG. 1B illustrates a bead with an embedded piezoelement.

FIG. 1B illustrates a detector particle 509 with an embedded piezoelement to detect HNWs. The detector particle 509 comprises particle halves 62 and a piezoelement 64 sandwiched between the two halves 64. The piezoelement 64 is preferably attached to the two halves 62 with an adhesive layer 66, where the adhesive layer 66 may comprise epoxy or other adhesive material. The particle halves 62 may be notched to allow for leads 65 from micro-miniature wiring associated with the piezoelement 64 to be embedded within the particle 509. The piezoelement 64 may have the wiring of the opposite faces of the piezoelement or in the same face by using a wrap around electrode and lead attachment. Preferably, the piezoelement 64 is calibrated to increase the accuracy of wave detection.

Figure 2A:
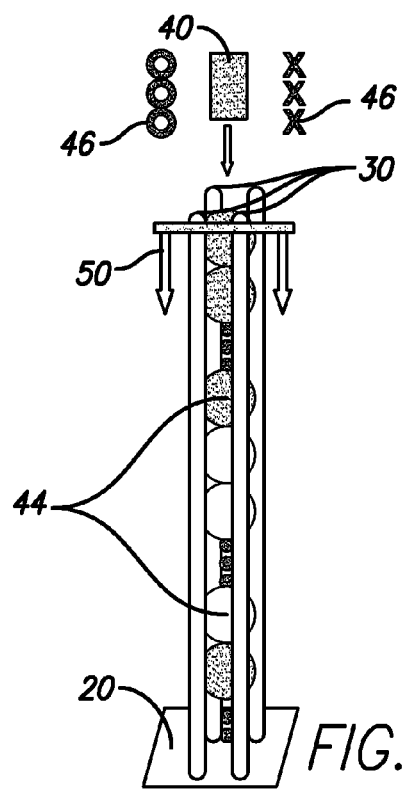
FIG. 2A illustrates a system for producing or detecting highly nonlinear waves.
Figure 2B:
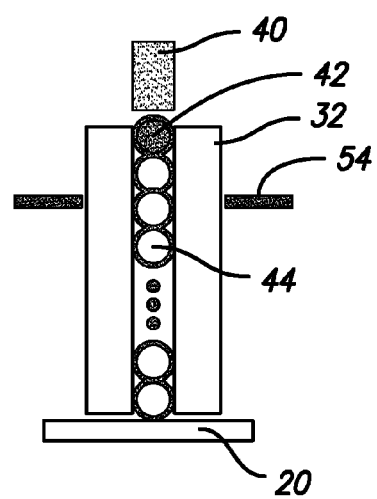
FIG. 2B illustrates a system for producing or detecting highly nonlinear waves.

Systems for producing or detecting HNWs are depicted in FIGS. 2A and 2B. FIG. 2A shows a three dimension view of an actuating and or sensing apparatus. As shown in FIG. 2A, four rods 30 are used to confine a chain of beads 44 that are used for the creation of highly nonlinear pulses for transfer to an element 20 or material to be tested. FIG. 2B shows a vertical cross-section of an apparatus similar to the one depicted in FIG. 2A where the four rods are replaced by a hollow cylindrical container 32 within which a chain of beads 44 is constrained. As discussed above, it may be useful to apply precompression for tuning the highly nonlinear waves. In FIG. 2A, element 50 depicts a system that may be used to apply static precompression. Element 50 may comprise a levitating ring magnet, a system to suspend controlled weights, a screw/load-cell controlled prestraining device, some other element or system that can compress the chain of beads 44, or some combinations of the elements and systems listed herein. As shown in FIG. 2B, a magnetic bead (or a bead holding suspended weights) 42 may be placed on top of the chain of beads 44 to allow for the application of static pre-compressive force. FIG. 2B also shows an outer holder 54 for handling and anchoring the hollow cylindrical container 30 on the element 20 or structure to be tested.

The constrained chain of beads 44 shown in FIGS. 2A and 2B may serve to produce or detect HNWs. For the production of such waves, a striker 40 may be used to initiate the formation of the HNW in the chain of beads 44. The striker 40 may be actuated through the use of an electromagnet 46 to move the striker 40 to strike the chain of beads 44. For example, the striker 40 may comprise a stainless steel ball lifted and released through an alternating magnetic field created by the electromagnet 46. The magnetic bead 42 shown in FIG. 2B may also serve as a means by which the chain of beads 44 are struck to produce pulses. A magnetically or an electro-magnetically controlled apparatus may be capable of generating pulses at frequencies greater than 20 kHz. Alternative embodiments may use a different activation mechanism such as a spring loaded system or a compressed air loaded system.

FIG. 3A is a schematic diagram representing the wave propagation of HNWs in a bulk highly nonlinear, weakly nonlinear or linear medium. A highly nonlinear pulse generator 10 (also referred to herein as a highly nonlinear actuator/exciter) generates a single or a train of highly nonlinear waves 14 that is directed into the element 20 or structure under test. FIG. 3A shows the propagation of the wave 14 through the element 20, which may comprise a bulk highly nonlinear, weakly nonlinear or linear medium. The propagating wave within the medium under testing may comprise linear stress waves and/or highly non linear waves. An output pulse 16 is received by a highly nonlinear receiver 12. FIG. 3B shows the generation of the single HNW 14 by the actuator 10 in the element 20, which may comprise a waveguide structure made of highly nonlinear, weakly nonlinear or linear medium. In FIG. 3B, the actuator 10 for HNWs is used also as sensing element for pulses 18 reflected by the waveguide edges and or defects.

One embodiment of the present invention comprises a method and system where a highly nonlinear actuator is used in combination with a classical receiver (such as an accelerometer, laser interferometer, piezogauge or other detectors known in the art). FIG. 4 depicts a system with this configuration. In FIG. 4, a highly nonlinear actuator/exciter 10 provides pulses to the element 20 that is undergoing testing with a potential defect 489. Element 20 may have a bulk or waveguide geometry and may comprise a highly nonlinear, weakly nonlinear or linear medium. The nonlinear actuator/exciter 10 has a striker particle 40 to initiate the formation of the HNW in the actuator 10. A first piezogauge 481 detects signals entering the element 20 under testing and a second piezogauge 482 detects the output signal after traveling in the tested element 20. A computer 90 may be used to process and store data to provide an analysis of the characteristics of the measured element 20. One or more calibrated piezogauges 64 disposed within elements of the actuator 10 may be used to detect the HNW propagating within the actuator/exciter 10 to provide the ability to additionally control or tune the actuator/exciter 10 to produce an HNW with desired characteristics.

Another embodiment of the present invention comprises a method and system where a classical impact echo/tap testing hammer (or other such methods or apparatus known in the art) is used in combination with a highly nonlinear receiver. FIG. 5 depicts a system with this configuration. In FIG. 5, a classical or a modally tuned hammer 96 is used to provide pulses to the element 20 or structure under test. Element 20 may have a bulk or waveguide geometry and may comprise a highly nonlinear, weakly nonlinear or linear medium. Typically, the hammer 96 may contain a piezogauge to detect and/or control pulses generated by the hammer 96. A nonlinear receiver 12 is coupled to the element 20 under test to receive pulses transmitted through the element 20 under test. The nonlinear receiver 12 may also be coupled to a piezogauge 482 which receives the HNW that has propagated through the nonlinear receiver 12. The nonlinear receiver 12 may also have one or more piezogauges 64 disposed within elements of the receiver 12 to detect the HNW propagating within the receiver 12. The receiver piezogauge 64 may be used in addition to or as an alternative to the piezogauge 482 to provide data on the characteristics of the element 20 under test. The receiver piezogauge 64 may also provide the capability to tune the response of the nonlinear receiver 12. A computer 90 may be used to collect and store data from the piezogauges 64, 482 and the hammer 96 to provide an analysis of the element or structure under test.

Still another embodiment of the present invention comprises a method and system where a highly nonlinear actuator is used in combination with a highly nonlinear receiver. FIG. 6 depicts a system with this configuration. In FIG. 6, a highly nonlinear actuator/exciter 10 provides pulses to the element 20 that is undergoing testing. As discussed previously, the actuator 10 may have one or more piezogauges 64 embedded within elements of the actuator 10 for HNW detection. A nonlinear receiver 12 is coupled to the element 20 under test to receive either highly nonlinear or linear pulses or a combination of both transmitted through the element 20 under test. Element 20 may have a bulk or waveguide geometry and may comprise a highly nonlinear, weakly nonlinear or linear medium. As discussed previously, the nonlinear receiver 12 may also have one or more piezogauges 64 disposed within elements of the receiver 12 to detect the HNW propagating within the receiver 12. The nonlinear receiver 12 may also be coupled to a piezogauge 482 which receives the HNW that has propagated through the nonlinear receiver 12 from the element 20 under test. A computer 90 may be used to collect and store data from the piezogauges 64, 482 to provide an analysis of the element or structure under test.

Figure 7:
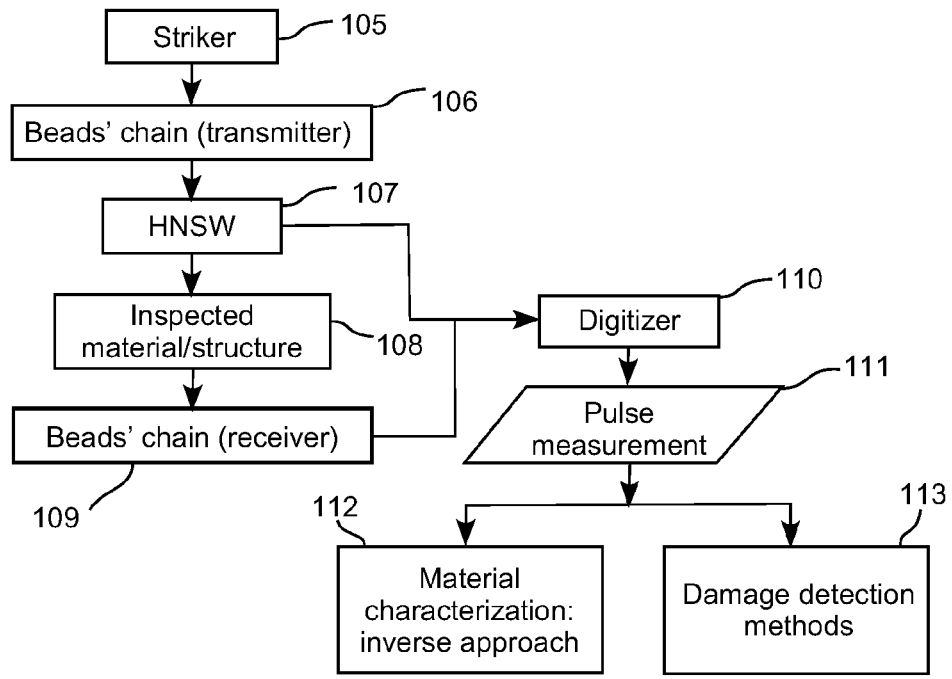
FIG. 7 is a flow chart showing steps of a method for performing nondestructive evaluations and structural health monitoring.

FIG. 7 is a flow chart showing steps of a method for performing nondestructive evaluations and structural health monitoring according to an embodiment of the present invention. In block 105, a striker is used to generate a pulse. In block 106, the pulse is coupled to a chain of beads serving as a transmitter for the formation of a HNSW. Block 107 depicts the detection and measurement of that wave within the transmitter and/or at the interface between the transmitter and the material or structure to be tested. Block 108 represents the propagation of the HNSW, or the propagation of linear bulk or linear guided waves within the material or structure to be inspected. Block 109 depicts the reception of one or more of those waves by a chain of beads with embedded piezoelement(s) acting as a receiver and the detection of the highly nonlinear pulses within the receiver and/or at the interface between the receiver and the material or structure under test. The signal detected prior to the material or structure under test and the signal detected after the material or structure under test are digitized at block 110 and measurements of the pulses made at block 111. Pulse measurement block 111 may include linear waves detected at the interface between the receiver and the material/structure under test. These nonlinear pulse measurements can then be used to characterize the material measured by an inverse approach, as shown in block 112, and/or detect damage within the structure or material, as shown in block 113.

Figure 8:
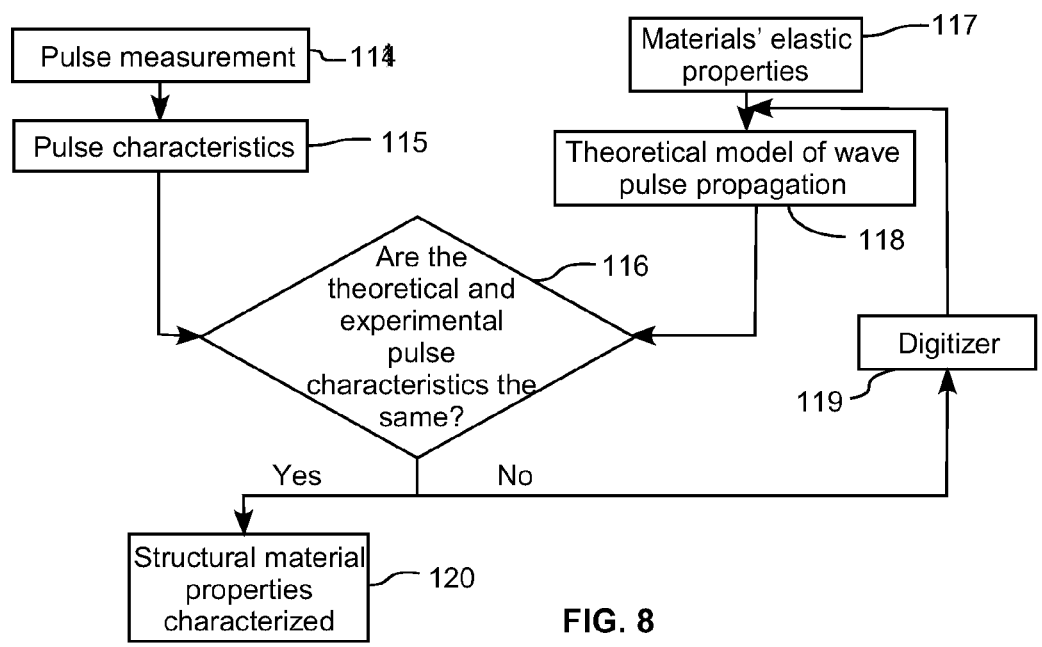
FIG. 8 is a flow chart showing steps for characterizing a material by using an inverse approach.

FIG. 8 is a flow chart showing steps for characterizing a material by using an inverse approach according to an embodiment of the present invention. In FIG. 8, block 114 represents the measurements of highly nonlinear pulses, such as those provided as shown in block 111 in FIG. 7. Calculations are then performed to determine the characteristics of the measured pulse or pulses as shown in block 115. Block 117 shows the collection of data related to the elastic properties of a large class of materials. Block 118 shows the calculation of a theoretical model of wave pulse propagation for a selected material type. Decision block 116 shows the comparison of measured pulse characteristics as provided by block 115 with theoretical characteristics as provided by block 118. If the measured and theoretical pulse characteristics are the same or nearly the same, block 120 shows that the properties of the measured material or structure can be characterized based on the measured pulses. If the measured and theoretical pulse characteristics do not sufficiently match, the differences can be provided to a digitizer 119 and then used to select a different material type for calculation of a theoretical model in block 118.

Figure 9:
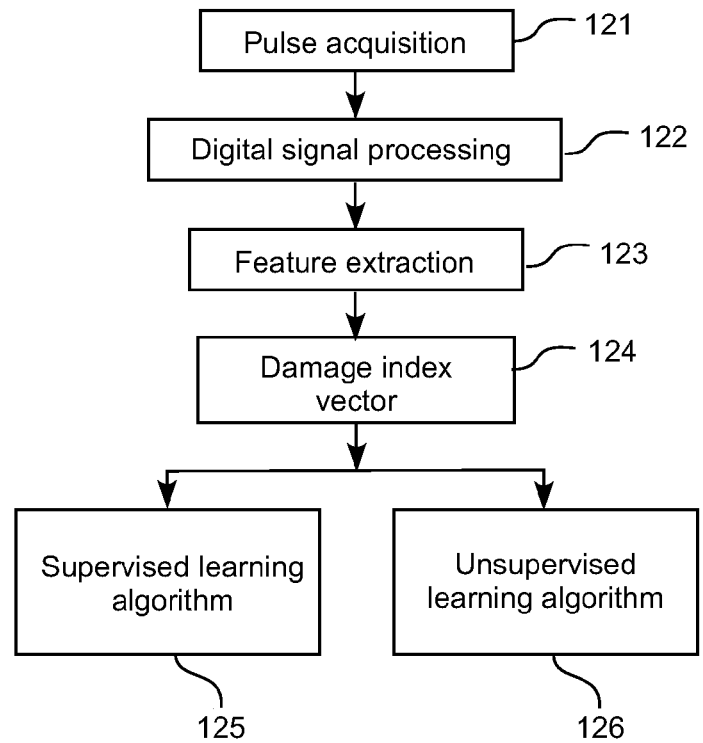
FIG. 9 is a flow chart showing steps for determining whether a material or structure has any damages based on highly nonlinear wave measurements.

FIG. 9 is a flow chart showing steps for determining whether a material or structure has any damage based on various excitations. In FIG. 9, block 121 represents the acquisition of measured pulsed data, such as that shown in block 111 in FIG. 7 and, for example, acquired by one of the methods depicted in FIGS. 4, 5 and/or 6. Block 122 shows the digital signal processing that may be performed on the pulse data to extract time domain related characteristics, frequency domain related characteristics, joint time-frequency domain characteristics, or other mathematical representations of the measured pulse data. Block 123 represents the calculations that may be performed to extract features of interest that may be used to identify and/or characterize damage. These features may be then used to construct a damage index vector, as shown in block 124, that may have one or more parameters related to damage identification. A supervised learning algorithm (as shown in block 125) or an unsupervised learning algorithm (as shown in block 126) may then be used to process the damage index vector and provide information as to the presence of defects or damage within the measured material or structure.

Figure 10:
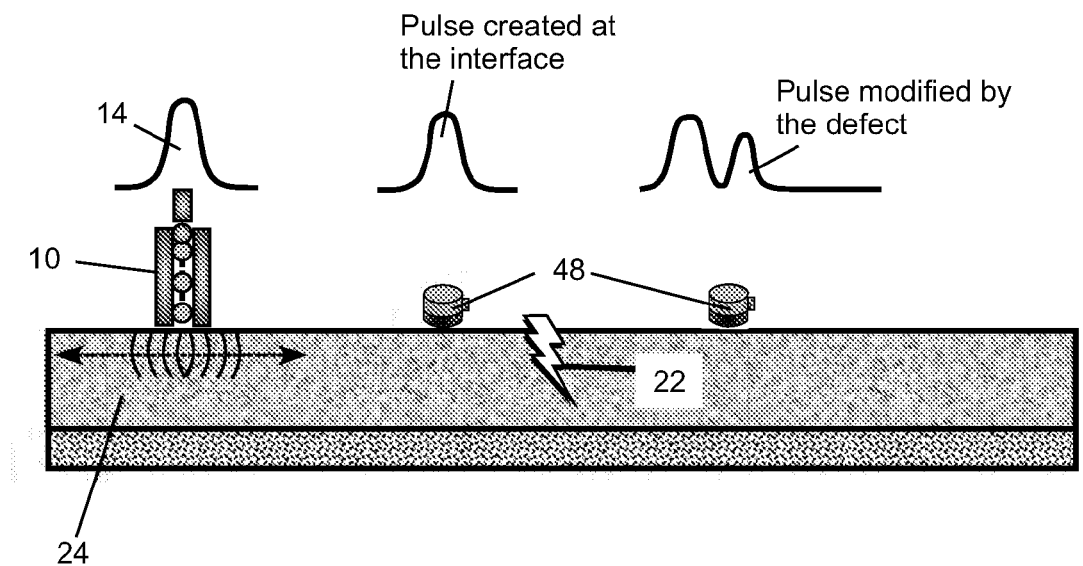
FIG. 10 illustrates the application of a highly nonlinear solitary wave to a damaged structure and propagation of the highly nonlinear solitary wave through the structure and a test setup to detect the damage.

FIG. 10 illustrates the application of a HNW to a damaged structure and propagation of the excited pulse through the structure and a test setup to detect the damage. In FIG. 10, a nonlinear actuator 10 forms and applies a HNW 14 to the element 24 under test. Element 24 can be a bulk, waveguide or semi-infinite structure made of highly nonlinear, weakly nonlinear, or linear medium. As depicted in FIG. 10, the element 24 may comprise a panel, plate, pavement, tile, flooring, etc. Sensors 48, such as accelerometers, laser interferometers, piezogauges, pressure sensors or other such detectors, detect and measure the propagation of the pulses through the element. The presence of a crack/void/deformation 22 in the element is expected to alter the amplitude and shape of the waves detected in output signals from the detectors 48. Analysis of the data obtained from the sensors should allow a user to locate and characterize the defect 22.

Figure 11:
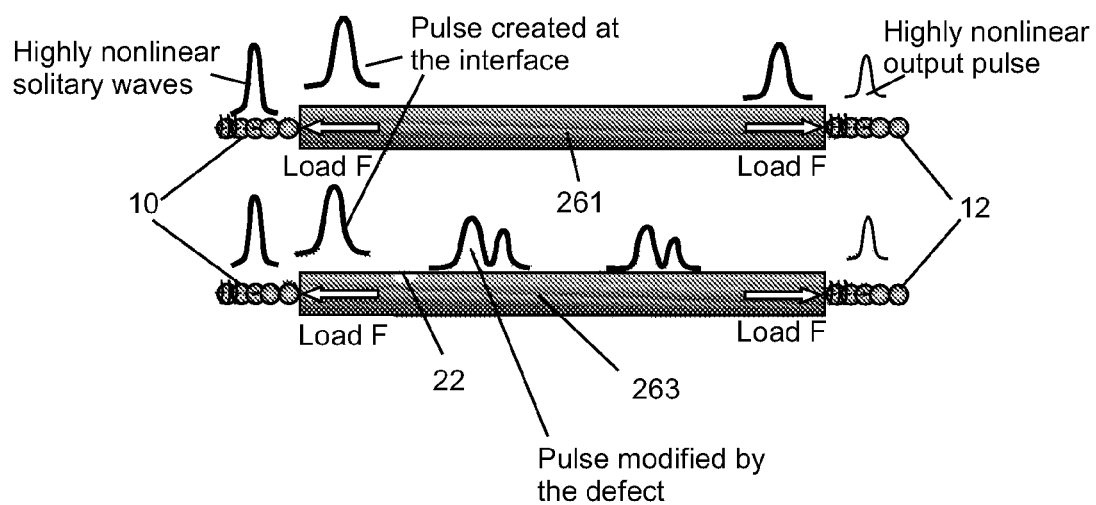
FIG. 11 depicts an undamaged seven wire steel strand and a damaged seven wire steel strand and the application of a highly nonlinear solitary wave thereto.

Embodiments of the present invention may also be used to detect defects in cylindrical waveguides made of highly nonlinear, weakly nonlinear, or linear medium. For example, FIG. 11 depicts a seven-wire steel strand 261 and a damaged seven wire steel strand 263. Such wire strands are widely used parts in prestressed concrete and cable-stayed suspension bridges. In FIG. 11, a nonlinear actuator 10 is used to apply the HNW and a nonlinear receiver 12 is used to detect the HNW. In the damaged strand 263, the presence of a prestress/temperature induced stress/strains and/or crack/void/deformation (as represented by the void 22) is expected to alter the amplitude and shape of the solitary waves detected by the nonlinear receiver 12. Alternative embodiments of the present invention allow for the detection of defects within cable configurations other than stranded steel.

Figure 12A:
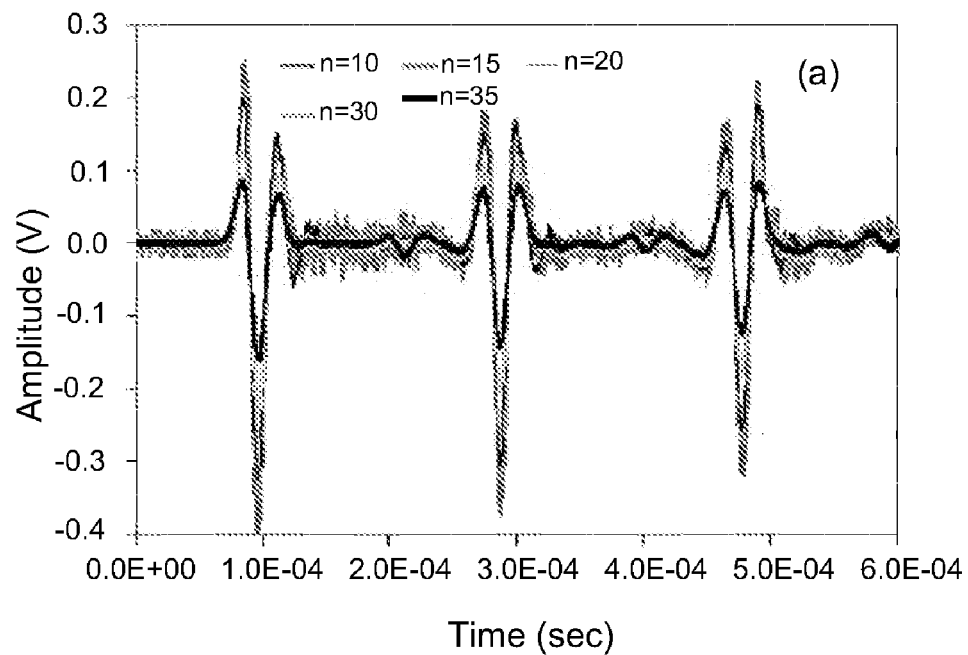
FIGS. 12A and 12B show experimental results where highly nonlinear solitary wave induced pulses are propagated within a steel rod.
Figure 12B:
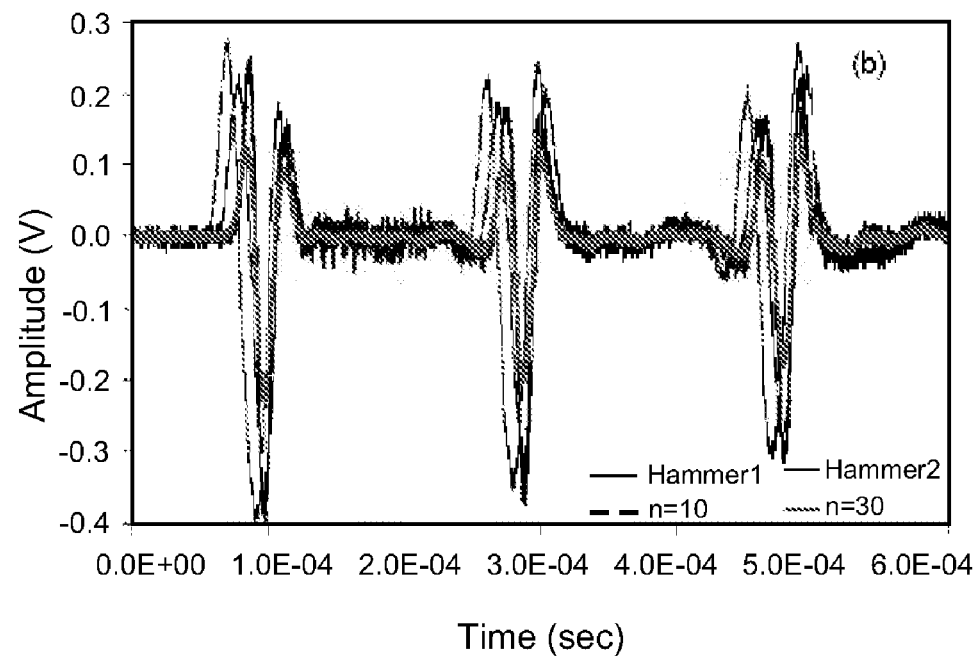

FIGS. 12A and 12B show experimental results where HNWs-induced pulses are propagated within a steel rod. In FIG. 12A, pulses were generated with a variable number (n) of beads into a chain of stainless steel beads. In FIG. 12B, pulses were generated by impacting a miniature hammer and by using n=10, 30 of HNW-inducing beads. As can be seen from FIGS. 12A and 12B, the time domain characteristics of the pulses change with the number of beads used to induce the HNW, indicating the tunability of the HNW actuator.

Figure 13A:
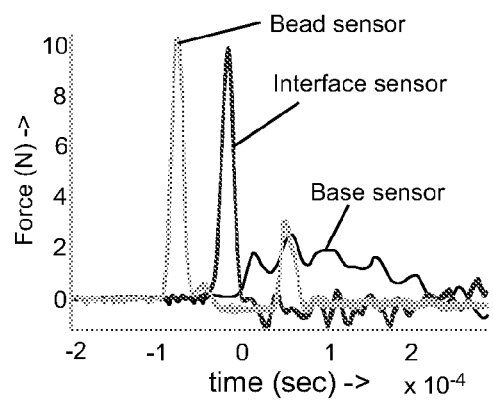
FIGS. 13A and 13B show experimental results where highly nonlinear solitary wave induced pulses are propagated within a steel rod using a test setup similar to that depicted in FIG. 4.
Figure 13B:
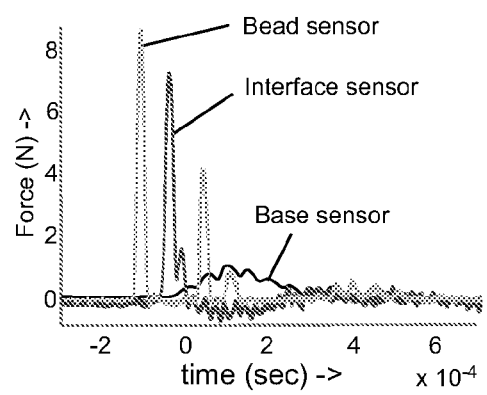
Figure 14A:
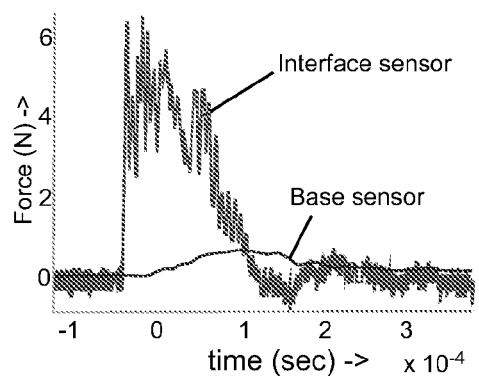
FIGS. 14A and 14B show experimental results where highly nonlinear solitary wave induced pulses are propagated within a steel rod using a test setup similar to that depicted in FIG. 4, but with only two sensors.
Figure 14B:
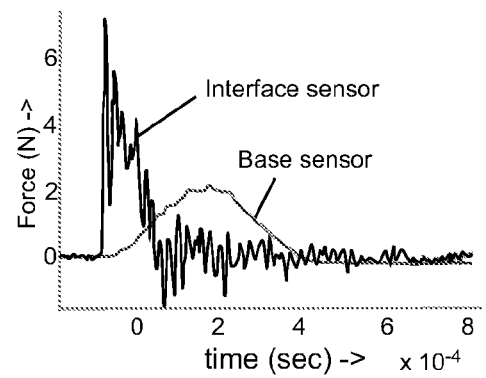

Experimental data shows that a HNW can be excited in a damaged and undamaged structure. The pulse detected after traveling in a damaged structure will differ from one detected after propagating through an undamaged structure. FIGS. 13A and 13B show experimental curves obtained for a test setup as shown in FIG. 4, where the element 20 under test is a steel rod. FIG. 13A depicts data obtained from positioning 4.76 mm diameter beads on a pristine steel rod, while FIG. 13B depicts data obtained from positioning 4.76 mm diameter beads on a damaged steel rod. Sensors were positioned in one of the central beads composing the chain (curve labeled "bead sensor" and corresponding to element 64 in FIG. 4), at the interface (corresponding to element 481 in FIG. 4) and at the base below the steel rod (corresponding to element 482 in FIG. 4). The impulses were generated by dropping a 0.45 g steel bead from a height of 3 cm on the top particle of the chain. FIGS. 14A and 14B show experimental curves obtained for a test set up similar to that shown in FIG. 4 where the element 20 under test is again a steel rod. However, sensors were positioned only at the interface and at the rod's base. FIG. 14A depicts data obtained from positioning 2.38 mm diameter beads on an undamaged steel rod and FIG. 14B depicts data obtained from positioning 2.38 mm diameter beads on a damaged rod. The impulses were generated dropping a 0.45 g steel bead from a height of 3 cm on the top particle of the chain.

Figure 15A:
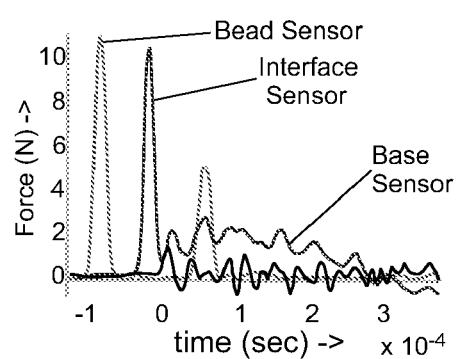
FIGS. 15A and 15B show time history results where highly nonlinear solitary wave induced pulses are propagated within a steel rod and precompression is used.
Figure 15B:
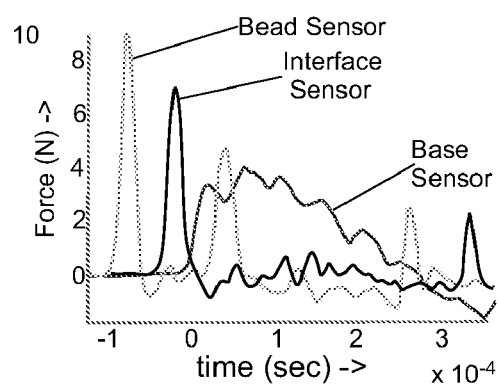
Figure 16A:
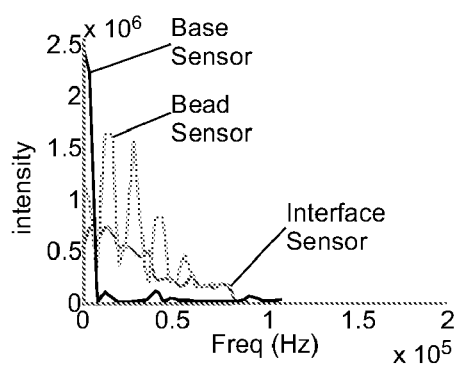
FIGS. 16A and 16B show frequency-intensity results where highly nonlinear solitary wave induced pulses are propagated within a steel rod and precompression is used.
Figure 16B:
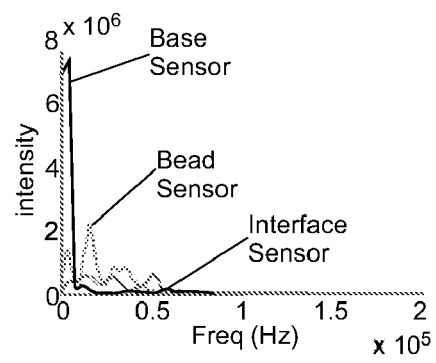

As discussed above, precompression may also serve to tune the HNW provided by a nonlinear actuator. FIGS. 15A, 15B, 16A and 16B illustrate the effect that precompression may have. FIG. 15A depicts time data obtained from positioning 20 vertically aligned stainless steel particles on top of a 4.76 mm diameter steel rod with added static precompression ($F_0$=2.38 N). The test setup was similar to that shown in FIG. 4, where sensors were positioned in one of the central beads composing the chain (curve labeled "bead sensor" and corresponding to element 64 in FIG. 4), at the interface (corresponding to element 481 in FIG. 4) and at the base below the steel rod (corresponding to element 482 in FIG. 4). FIG. 15B shows time data obtained with a similar set up using a damaged rod. FIG. 16A shows intensity verses frequency data obtained from measurements made from the pristine rod, while FIG. 16B shows intensity versus frequency data obtained from the damaged rod.

Figure 17:
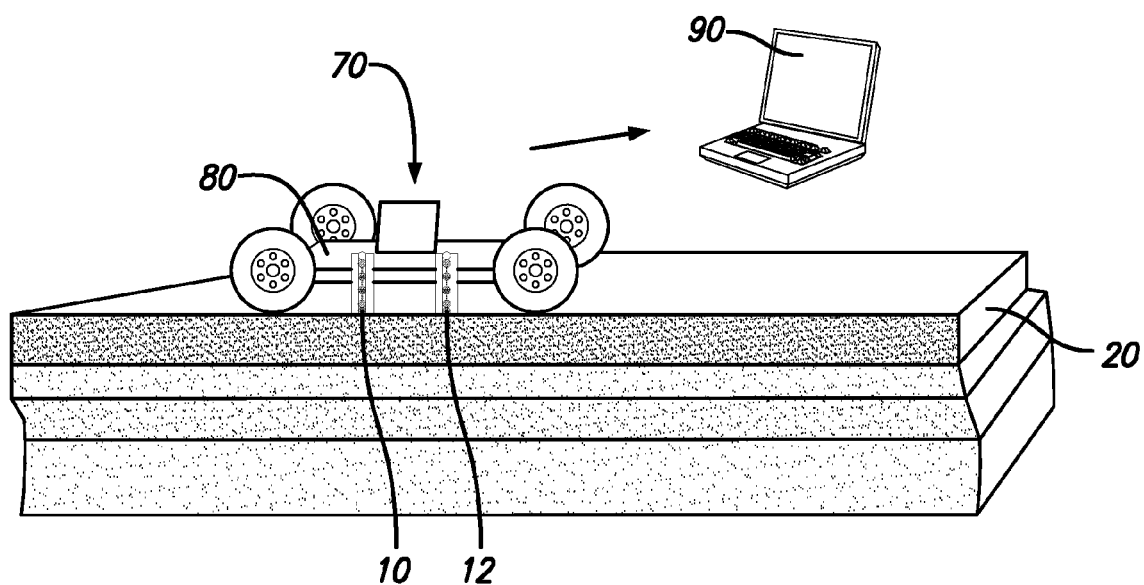
FIG. 17 shows a system for automated evaluation and monitoring of pavements, railroads, floor spaces and other such structures.

An embodiment of the present invention may comprise a method and system for automated evaluation and monitoring of pavements, railroads, floor spaces and other such structures. FIG. 17 is a schematic view of such an embodiment. In FIG. 17, a trolley 80 has both a nonlinear actuator 10 and a nonlinear receiver 12 mounted on it. The nonlinear actuator 10 and a nonlinear receiver 12 are both mounted in a fashion that allows them to contact the structure 20 under test. In operation, the nonlinear actuator 10 provides highly nonlinear pulses and the nonlinear receiver 12 detects the highly nonlinear pulses. As indicated above, alternative embodiments may use classical impact methods known in the art (such as an impact hammer) instead of the nonlinear actuator 10 to provide pulses for detection by the nonlinear receiver 12. Other embodiments may use the nonlinear actuator 10, but the pulses from the actuator 10 may be detected by classical detection methods or apparatus instead of the nonlinear receiver 12.

In the system depicted in FIG. 17, the computer 90 may provide for control over the nonlinear actuator 10 and the nonlinear receiver 12 and also control the motion of the trolley. Signals to and from both the nonlinear actuator 10 and the nonlinear receiver 12 may be coupled to a data collection station 70 that may be coupled, either wirelessly or with a wired connection, to the computer 90. For example, the data collection station may comprise a unit from National Instruments utilizing PXI technology running LabView® or analogous hardware/software. The computer 90 may comprise a laptop computer which could then be configured to form a client-server Ethernet link with the data collection station 70. The data collection station 70 may be configured to control the generation of test pulses by the nonlinear actuator 10, acquire signals from the nonlinear receiver 12, process the signals to limit noise, and produce a real-time quality index for the monitored structure 20. The computer 90 may then be used to start and stop the acquisition, modify the pulse and pulse processing settings, monitor the results in real-time, and provide report windows.

The system depicted in FIG. 17 may provide a user the ability to exploit HNW induced pulses propagating across and along the thickness of the structure 20 and within the structure 20 itself. While FIG. 17 only shows a single actuator 10/receiver 12 pair, multiple actuator/receiver pairs may be deployed to form a grid that covers large sections of the structure 20 at once. This may speed up the rate at which the structure 20 can be inspected and also improve the quality of the inspection.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising step(s) for . . . "

What is claimed is:

1. A method for performing an inspection of an element or structure comprising:
    generating an inspection pulse;
    directing the inspection pulse into the element or structure to be inspected;
    directing the inspection pulse after it has propagated through at least a portion of the element or structure to be inspected into a nonlinear receiver; and
    detecting the inspection pulse after it has propagated through at least a portion of the nonlinear receiver,
    wherein the nonlinear receiver comprises a chain of spherical particles, wherein each particle in the chain of spherical particles is in linear contact with adjacent particles in the chain.

2. The method according to claim 1, wherein the particles in the chain of particles are linearly constrained and are compressed in the linear direction.

3. The method according to claim 1, wherein detecting the inspection pulse comprises detecting the inspection pulse with at least one particle in the chain of particles comprising at least one of the following detection elements: a wave detection element; a pressure detection element; an acceleration detection element, or a displacement detection element.

4. The method according to claim 1, wherein detecting the inspection pulse comprises directing the inspection pulse into an end of the chain of particles adjacent to the element or structure to be inspected and detecting the inspection pulse at an end of the chain of particles opposite to the end adjacent to the element or structure to be inspected.

5. A system for inspecting an element or structure comprising:
    a pulse actuator, wherein the actuator is configurable to apply pulses to the element or structure to be inspected, and
    a nonlinear receiver configurable to detect pulses from the actuator propagating through at least a portion of the element or structure to be inspected,
    wherein the nonlinear receiver comprises a chain of spherical particles, wherein each particle in the chain of spherical particles is in linear contact with adjacent particles in the chain.

6. The system according to claim 5, wherein the particles in the chain of are linearly constrained and are compressed in the linear direction.

7. The system according to claim 5, wherein at least one particle in the chain of particles comprises at least one of the following detection elements: a wave detection element; a pressure detection element; an acceleration detection element, or a displacement detection element.

8. The system according to claim 5, wherein the nonlinear receiver comprises at least one detection element disposed at an end of the chain of particles, wherein the detection element comprises at least one of the following detection elements: a wave detection element; a pressure detection element; an acceleration detection element, or a displacement detection element.

* * * * *